United States Patent [19]

Spalten

[11] 4,059,901
[45] Nov. 29, 1977

[54] PORCELAIN FUSED TO METAL DENTURE TOOTH RETAINER

[76] Inventor: Robert Spalten, 745 Fifth Ave., New York, N.Y. 10022

[21] Appl. No.: 606,190

[22] Filed: Aug. 20, 1975

[51] Int. Cl.$^2$ ............................................. A61C 13/00
[52] U.S. Cl. ......................................................... 32/8
[58] Field of Search ................................. 32/8, 2, 9, 10

[56] References Cited

U.S. PATENT DOCUMENTS

| | | | |
|---|---|---|---|
| 1,260,118 | 3/1918 | Zurcher-Hinnew | 32/10 R |
| 2,202,712 | 5/1940 | Myerson | 32/8 |
| 3,052,982 | 9/1962 | Weinstein et al. | 32/8 |

FOREIGN PATENT DOCUMENTS

| | | | |
|---|---|---|---|
| 16,169 of | 1911 | United Kingdom | 32/10 R |
| 380,991 | 1932 | United Kingdom | 32/10 R |

Primary Examiner—Robert Peshock
Attorney, Agent, or Firm—Harry Ernest Rubens

[57] ABSTRACT

A porcelain denture tooth for attachment to the denture plastic base, mounted to the gums, made with a unitary thinwalled metal embedded support, U-shaped in cross-section, embedded in the denture tooth body, with portions of the U-shaped metal retainer extending outside the tooth body to form ahead portion for attachment to the denture base.

4 Claims, 2 Drawing Figures

PORCELAIN FUSED TO METAL DENTURE TOOTH RETAINER

This invention relates to the manufacture of denture teeth, mounted to a plastic base, molded to the gums, to provide support for the denture teeth, when natural roots are missing.

The denture teeth are presently made of porcelain or plastic, cemented or mechanically interlocked to the metal support pins. Such denture teeth are subject to fracture in an area leading from the denture pin to the nearest porcelain surface.

Accordingly, the principle object of the invention is to provide a denture tooth construction made of porcelain, which will reduce the high local stresses between the metal support and the porcelain, and thus eliminate the possibility of fracture.

Other objects are, to provide a novel form of denture support pin or retainer which is fused to the porcelain to provide the increased contact area with the porcelain to reduce unit stresses; to provide thin-walled denture retainers which will reduce the weight of the retainer with appreciably increased structural strength over conventional pins; and to provide the foregoing features in a porcelain denture tooth without adding to its weight or detracting from the esthetic and hygienic requirement in the mouth.

These and other objects and features of the invention are obtained, and my new results accomplished, as will be apparent from the denture teeth described in the following specifications, particularly pointed out in the claims, and illustrated in the accompanying drawing in which:

I have discovered that by using a denture retainer with a large porcelain surface in relation to its embedded weight, it is possible to produce a porcelain fused denture that is relatively light in weight and fracture free.

Figure 1:
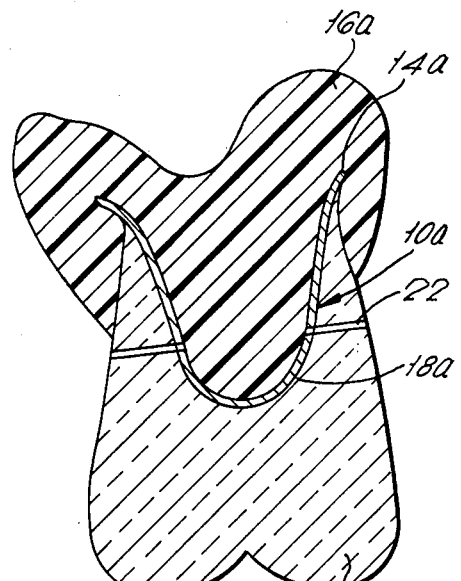
FIG. 1 is a longitudinally sectioned view of a denture assembly showing my new denture retainer fused to the porcelain body.

As shown in FIG. 1, the denture retainer 10a comcomprises a thin walled sheet, U-shaped in cross-section embedded in the porcelain body 20a, portions thereof, 14a extending out of the porcelain body for attachment to the plastic denture base 16a. The bottom of the metal retainer 10a, designated as 18a, extends towards the biting surfaces of the porcelain body, sufficiently to reinforce the body against cracking, by providing a relatively large area of contact between the retainer and the porcelain. An aperture 22 may be drilled through the porcelain tooth and retainer from the mesial to distal sides to provide additional retention by allowing the plastic denture base material to enter the drilled tooth.

Figure 2:
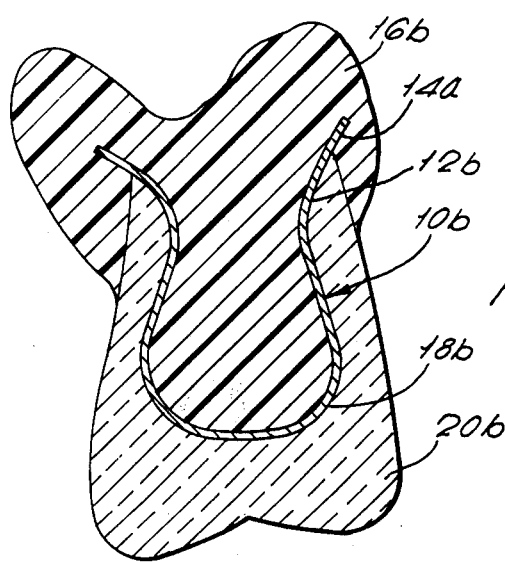
FIG. 2 is a similar view showing a modified form of denture retainer.

In FIG. 2. I have shown a modification of the denture retainer with an enlarged bulbous shape 18b forming a neck portion 12b. This will permit further retention of the porcelain metal tooth to base 16b. The remaining reference numerals are similarly numbered as in FIG. 1. but with a "b" instead of an "a" letter designation.

In conventional denture construction, the headed, dumb-bell shaped pin caused high unit stresses leading to fractures when in use with mechanically mounted porcelain teeth.

When the porcelain is fused to the retention plate of the present invention, fractures will not occur. This is because the unit stresses will not build up to dangerous levels with the new enlarged area of fused contact between retainer and porcelain.

All the forms shown are characterized by thin walls, and with maximum area of contact for the fused connection between retainer and porcelain. The large surface area is maximum for its embedded weight.

The denture retainer of the invention may be made of any metal that can be fused to the porcelain. For economy, it may be made of non-precious metal, such as stainless steel, or nickel chrome alloys.

One technique for applying the invention is to apply an opaque coating to the cleaned metal surface of the retainer, for preventing the dark color of the non-precious metal from being visible from the front of the tooth. This opaque material may consist of opaqified porcelain applied in paste form and slowly baked in a rising temperature to about 2000° F.

A porcelain material is then applied that has an adjusted coefficient of expansion compatible with that of the metal of the retainer. This will prevent inner separation of the two layers during the cooling process.

The porcelain material may comprise aluminum silicate, potassium aluminum silicate, with various binders and pigments which may be desired for color. The material is powdered and formed into a putty-like mass. Such porcelains are available commercially.

Depending on the metal used, it may be desired to apply a thin layer of ceramic gold cream to the cleaned wall of the retainer. Thereafter the coated retainer is heated to about 200° F. to form a fused adhering coating on the retainer that can be fused to the porcelain body. It may be desirable, to insure a good fusion between retainer and porcelain, to apply the porcelain in the form of layers which are individually baked to the desired temperatures to insure good fusion. The temperatures will vary depending on whether low fusing, medium fusing, or high fusing porcelains are used.

The advantage of the invention is that the denture retainer may be made of standard shapes, suitable for incisors, bicuspids or molars. This, plus the standard molded porcelain teeth shapes, eliminates the necessity for custom procedures, thus reducing time and cost. The denture retainer may be formed from sheet metal, further reducing costs.

I have thus described my invention, but I desire it understood that it is not confined to the particular forms or uses shown and described, the same being merely illustrative, and that the invention may be carried out in other ways without departing from the spirit of my invention, and that equivalent instrumentalities may be employed since the particular embodiments herein shown and described are only some of the many that can be employed to obtain my objects and accomplish my results.

I claim:

1. A denture tooth for attachment to a denture appliance having a molded denture base conforming to the gum areas of the mouth, said denture tooth comprising a body and an extending metal retainer made of a single piece of metal terminating in a head portion for attachment to the denture base, said metal retainer having embedded in said body, a metal retention portion, U-shaped in cross-section, extending longitudinally towards the biting edge of the tooth for the major portion of the tooth length, providing a large engaging surface to increase its retention and reinforcing characteristics with the tooth body, the anterior and posterior portions of the U-shaped cross-section extending from the tooth body to form the head portion for attachment to the denture base.

2. The denture tooth of claim 1 wherein the embedded portion of the retainer is hollow.

3. The denture tooth of claim 1 wherein the head portion comprises a peripherally extending flange.

4. The denture tooth of claim 1 wherein the embedded portion is perforated.

* * * * *